US009072614B2

(12) United States Patent
Starkey et al.

(10) Patent No.: US 9,072,614 B2
(45) Date of Patent: Jul. 7, 2015

(54) ARTIFICIAL HAND

(71) Applicant: Season 4, LLC, Charlotte, NC (US)

(72) Inventors: Michael Starkey, Charlotte, NC (US);
Thomas James Philpott, Charlotte, NC (US)

(73) Assignee: SEASON 4, LLC, Charlotte, NC (US)

( * ) Notice: Subject to any disclaimer, the term of this patent is extended or adjusted under 35 U.S.C. 154(b) by 13 days.

(21) Appl. No.: 13/844,394

(22) Filed: Mar. 15, 2013

(65) Prior Publication Data

US 2013/0345828 A1 Dec. 26, 2013

Related U.S. Application Data

(60) Provisional application No. 61/663,568, filed on Jun. 23, 2012.

(51) Int. Cl.
A61F 2/58 (2006.01)
B25J 15/08 (2006.01)
B25J 15/04 (2006.01)
B25J 15/00 (2006.01)

(52) U.S. Cl.
CPC ............ *A61F 2/586* (2013.01); *A61F 2002/587* (2013.01); *B25J 15/083* (2013.01); *B25J 15/0475* (2013.01); *B25J 15/086* (2013.01); *B25J 15/0009* (2013.01); *A61F 2/583* (2013.01)

(58) Field of Classification Search
CPC .... B25J 15/0475; B25J 15/083; B25J 15/086; B25J 15/0009; B25J 15/028
USPC ..................................................... 623/63–64
See application file for complete search history.

(56) References Cited

U.S. PATENT DOCUMENTS

| 1,298,502 | A |   | 3/1919 | Henning |       |
|-----------|---|---|--------|---------|-------|
| 2,285,885 | A | * | 6/1942 | Becker  | 623/64|
| 2,425,154 | A | * | 8/1947 | Hibbard | 623/64|
| 3,694,021 | A |   | 9/1972 | Mullen  |       |
| 4,258,441 | A |   | 3/1981 | Bell    |       |
| 4,865,613 | A | * | 9/1989 | Rizzo   | 623/65|
| 7,655,051 | B2|   | 2/2010 | Stark   |       |

FOREIGN PATENT DOCUMENTS

RU       2 103 950 C1  *  2/1998  ............... A61F 2/54

* cited by examiner

Primary Examiner — David H Willse
(74) Attorney, Agent, or Firm — Tillman Wright, PLLC; Chad D. Tillman; Jeremy C. Doerre

(57) ABSTRACT

An artificial hand includes a palm component having a plurality of finger sockets. A plurality of artificial fingers are received in a snap-fit engagement in the plurality of finger sockets of the palm component. At least one of the plurality of fingers has a locking slide including a plurality of locking teeth and a reverse lock including a locking cam, wherein the locking cam is engaged with the locking teeth to lock the finger in a preferred position. In a feature of the disclosed hand, the artificial finger further comprises a connector attached to the reverse lock, such that a tension applied to the connector through the palm component lifts the locking cam, disengaging the locking cam from the locking teeth of the lock slide.

18 Claims, 4 Drawing Sheets

ARTIFICIAL HAND

CROSS-REFERENCE TO RELATED APPLICATION

The present application is a U.S. nonprovisional patent application of, and claims priority under 35 U.S.C. §119(e) to, U.S. provisional patent application Ser. No. 61/663,568, filed Jun. 23, 2012, which provisional patent application is incorporated by reference herein. The present application hereby incorporates herein by reference the entire disclosure of Exhibit 1 attached as an appendix hereto, which represents the disclosure of this priority provisional application.

COPYRIGHT STATEMENT

All of the material in this patent document, including source code, is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

COMPUTER PROGRAM LISTING

Submitted in U.S. provisional patent application Ser. No. 61/663,568, filed Jun. 23, 2012 via the USPTO's electronic filing system, and incorporated herein by reference, are computer program files including instructions, routines, and/or other contents of several computer programs. A table setting forth the name and size of each file included in the computer program listing is included below.

| File Name | Creation Date | Size in Bytes | Description |
|---|---|---|---|
| ASCIFY.txt | 6/23/2012 16:26 | 37473 | assembly source code |
| EDRAWING.TXT | 6/23/2012 16:25 | 1551822 | eDrawing file |
| readme.txt | 6/23/2012 16:26 | 2649 | instructions |

A first of these files, "readme.txt", contains instructions for utilizing a second of the files "ascify.txt" to extract information from "edrawing.txt". "edrawing.txt" is an .easm eDrawing file that has been converted to ascii format. This file can be converted back to binary format utilizing a assembly conversion program source code for which is contained in "ascify.txt". The readme file includes instructions for compiling and running this conversion program, as well as instructions for converting "edrawing.txt" into an .easm eDrawing file. This .easm eDrawing file can be viewed using SolidWorks' eDrawings program, currently available for free download at http://www.solidworks.com. This .easm eDrawing file discloses and illustrates components of a preferred embodiment of an artificial hand in accordance with the present invention, including aspects and features shown in the drawings. Moreover, it will be appreciated that a coil spring is provided at one of the joints of each digit for biasing the digit toward the closed position in the embodiment represented by the eDrawing; preferably a coil spring is provided at each joint of each digit.

BACKGROUND OF THE INVENTION

The present invention relates to a device that mimics the hand and, more particularly, to an artificial hand.

Artificial hands are well-known in the art. Many artificial hands are biased open, in that they are at rest in the open position. These hands have an artificial look, in that normal human hands rest in a curved, closed position rather than a flat, spread open position. Further, many of the uses for an artificial hand are for the closed position, such as gripping, lifting or carrying an object. For example, a mechanical hand amusement device is disclosed in U.S. Pat. No. 4,315,650, which discloses articulated digits biased in the open position.

Artificial hands that are biased closed are also known. Such hands are disclosed, for example, in U.S. Pat. Nos. 7,655,051; 5,200,679; 4,685,924; 2,561,383; 2,500,614; 2,285,885; and 1,742,269.

U.S. Pat. No. 7,655,051 is owned by Applicant and is incorporated herein by reference.

While there are numerous artificial hands as described above, there nevertheless is believed to be a need for improvement over such artificial hands. One or more aspects or features of the present invention are believed to represent such an improvement.

SUMMARY OF THE INVENTION

The present invention includes many aspects and features. Moreover, while many aspects and features relate to, and are described in, the context of an artificial hand for use by a person, the present invention is not limited to use only in such context, as will become apparent from the following summaries and detailed descriptions of aspects, features, and one or more embodiments of the present invention.

In a first aspect, an artificial hand comprises a palm component including a plurality of finger sockets for receiving a plurality of artificial fingers, and a plurality of artificial fingers engaged in a snap-fit manner in the plurality of finger sockets on the palm component. At least one of the plurality of fingers comprises a locking slide including a plurality of locking teeth and a reverse lock including a locking cam, wherein the locking cam is engaged with the locking teeth to lock the finger in a preferred position. In a feature of the disclosed hand, the artificial finger further comprises a connector attached to the reverse lock, such that a tension applied to the connector through the palm component lifts the locking cam, disengaging the locking cam from the locking teeth of the lock slide.

In another aspect of the invention, an artificial hand includes articulating digits, wherein at least one of the articulating digits is removable by the user for replacement with another digit.

In another aspect, an artificial hand includes articulating digits, wherein at least one of the articulating digits is secured against movement toward an open position unless and until a user actuates the digits to move toward respective open positions.

In another aspect, an artificial hand includes articulating fingers, wherein at least one of the articulating finger is locked against movement toward an open position unless and until all fingers are actuated by the user to move toward respective open positions.

Another aspect comprises a method of making an artificial hand in accordance with one or more aspects and features disclosed herein.

Another aspect comprises a method of operating an artificial hand in accordance with one or more aspects and features disclosed herein.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
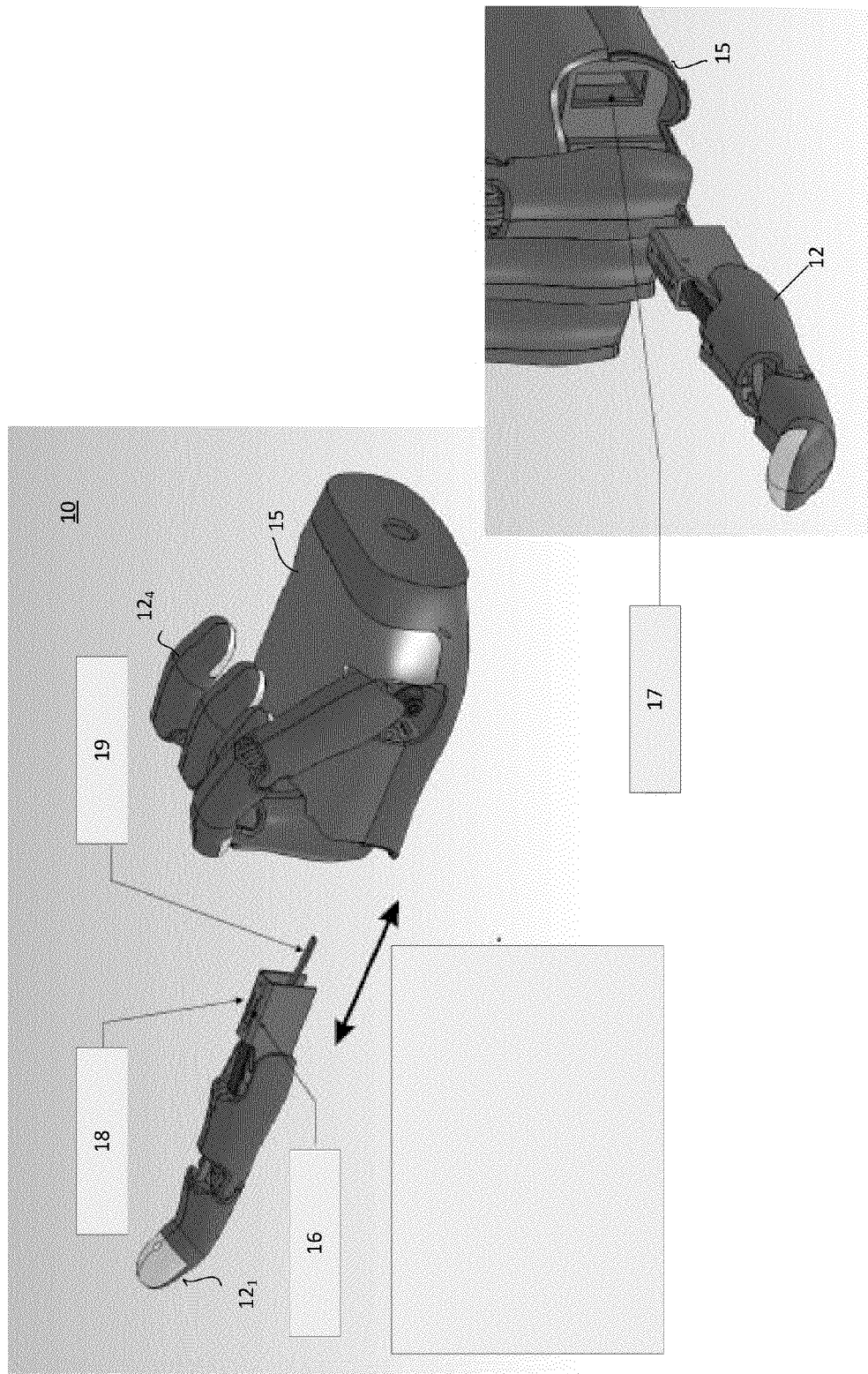
FIG. 1 illustrates an exemplary artificial hand in accordance with the present invention.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

Turning now to FIG. 1, an aspect of the invention is illustrated relating to removable fingers $12_{1 \ldots 4}$, wherein each digit comprising a finger $12_1$ of an artificial hand 10 is removably connected to the palm component 15 of the artificial hand. In particular, the finger $12_1$ is received within a finger socket 17 of the palm component 15 and preferably is held in a snap-fit retention therein between a seat lock 16 of a finger post 18 of the finger 12, and the geometry of the finger socket 17.

The snap-fit engagement permits the finger 12 to be readily withdrawn and replaced with another finger 12 by a user. Such replacement may be desired if a finger 12 is damaged or otherwise requires maintenance. To the extent a finger 12 includes a different texture or surface for performing a particular function, a finger 12 can be easily replaced or switched out, as desired, when the function is to be performed. Moreover, each of the fingers 12 preferably are interchangeable with each other, including the index, ring, middle, and pinkie fingers.

When a finger 12 is to be withdrawn from a finger socket 17, or inserted into a finger socket 17, a palm covering component (not shown) preferably is removed to permit access to the interior of the palm component 15. In this respect, a zip-tie type body 203, illustrated in FIG. 2, extending from the finger can be readily engaged (during insertion of the finger) or disengaged (during removal of the finger) from an internal mechanism which receives the zip-tie type body 203.

The mechanism of receiving and releasably retaining a finger within a finger socket, and the mechanism for engaging the zip-tie type body of the finger, are further shown and disclosed in the eDrawing of the computer program listing, incorporated herein by reference.

Figure 2:
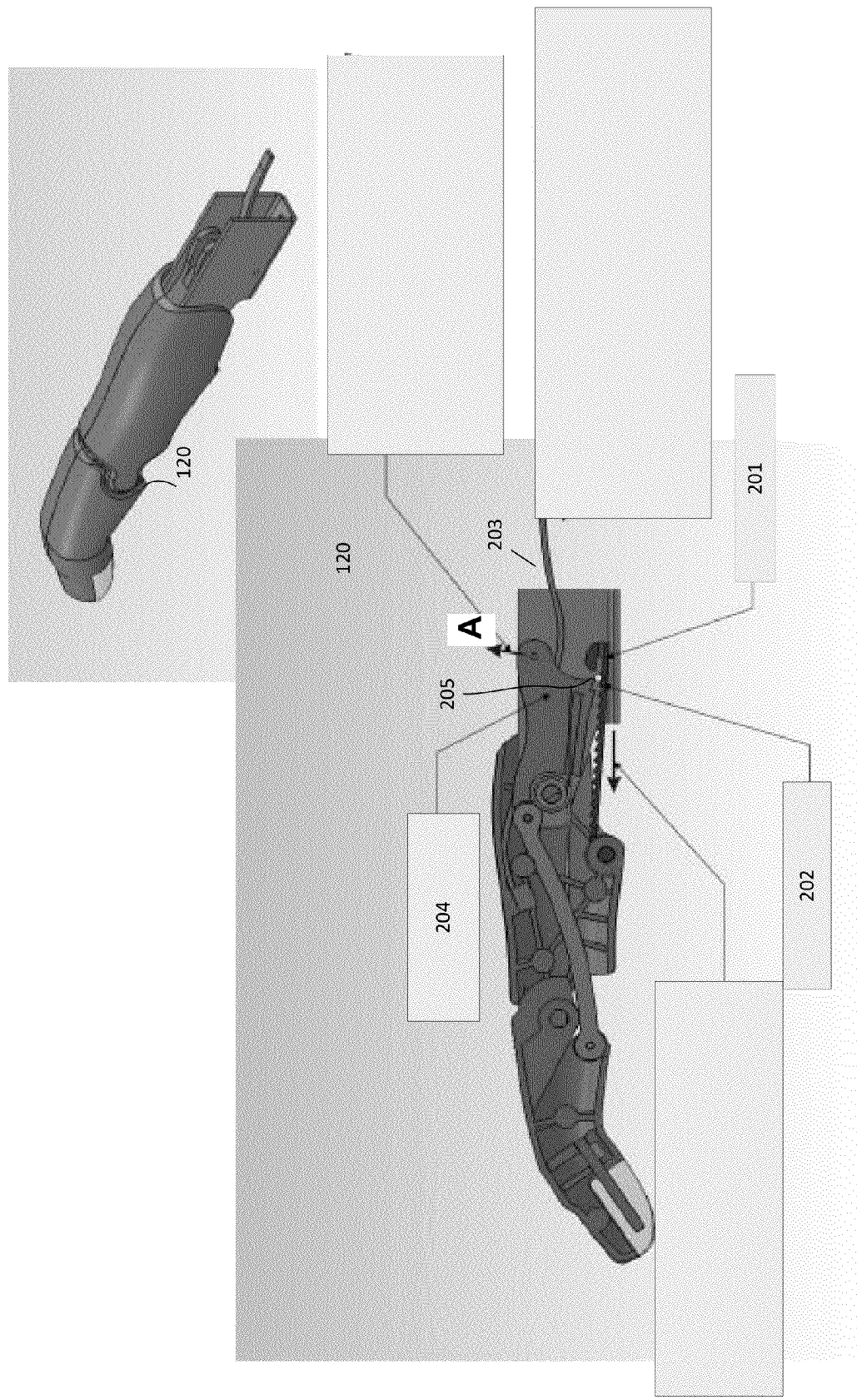
FIG. 2 illustrates an cross-sectional view of an exemplary artificial finger of the artificial hand shown in FIG. 1.

With regard to FIG. 2, another aspect relating to finger locking is illustrated. The finger 120 comprises the zip-tie type body 203, a reverse lock 204, and a lock slide 201. The reverse lock 204 includes a locking cam 205. The lock slide 201 includes a plurality of locking teeth 202, engaged with the locking cam 205, disclosed above. In particular, when a user applies voluntary force to open the fingers via a hand mechanism (not shown), tension is applied to the zip-tie body 203 which, in turn, tends to lift an end of the reverse lock 204 away from the locking teeth 202 of the lock slide 201, as shown by the arrow A. This lifting causes the locking cam 205 of the reverse lock 204 to disengage from the locking teeth 202 of the lock slide 201, thereby permitting the finger 120 to move toward a fully open position.

When a user does not apply force for purposes of extending the digits, i.e., moving each of the digits respectively toward a fully open position, each digit is precluded by engagement of the locking cam 205 with the locking teeth 202 from moving toward the fully open position. This locking action of each digit 120 enables each digit 120 to better grasp and lift or pull an object; otherwise, the force of gravity—or other counter force to lifting or pulling—results in the digits 120 opening once the respective force of the coil springs (not shown) of the digits has been overcome.

Figure 3:
FIG. 3 illustrates user selectable grip formations of the exemplary artificial fingers shown in FIGS. 1 and 2.

With regard to FIG. 3, user selectable grip formations of the digits are shown. It will be appreciated that the thumb is rotatable between a first position (thumb position 1 in FIG. 3) and a second position (thumb position 2 in FIG. 3), and that in each of these two thumb positions, two grip formations are shown. Thus, when the thumb is in thumb position 1 and the fingers are closed, a "power" grip formation of the digits is achieved; when the thumb is position 1 and the middle, ring and pinky fingers are closed with the index finger partially extended such that the tip engages the tip of the thumb, a "fine" grip formation of the digits is achieved; when the thumb is in thumb position 2 and the fingers are closed, a "lateral" grip formation of the digits is achieved; and when the thumb is position 2 and the middle, ring and pinky fingers are closed with the index finger fully extended, a "typing" grip formation of the digits is achieved.

Figure 4:
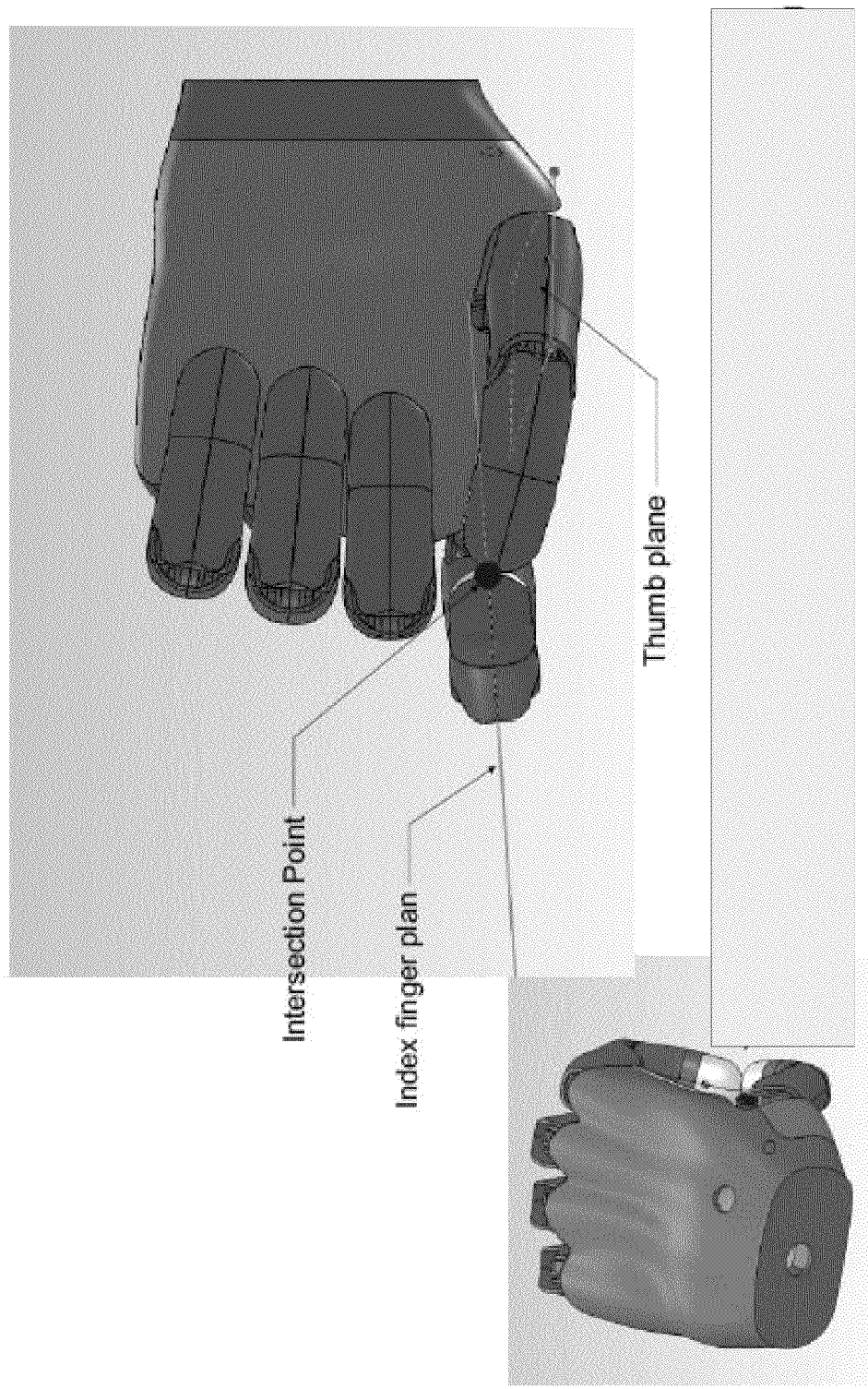
FIG. 4 illustrates a fine grip formation of the exemplary artificial fingers shown in FIGS. 1 and 2.

It will further be appreciated that, as shown in FIG. 4, when the fine grip formation of the digits is utilized, the index finger and thumb alignment planes are oriented to allow easy line of sight to an object being picked up when the palm is facing the user.

As will be appreciated from the disclosure herein, the present invention relates to a prosthetic hand or robotic hand having more than one articulated digit, wherein the digits are biased toward a closed position, and wherein, when activated, the digits move from the closed position toward the open position.

Furthermore, as shown in the eDrawing and the drawings, the digits preferably include pads that are exchangeable with other pads and that have different durometers for different object grasping and holding performance characteristics.

Additionally, in a preferred embodiment, the artificial hand can be covered by a glove or other covering to give it a natural appearance. Further, the digits can be covered by a synthetic material to give it greater gripping ability. A polymeric, resinous or rubber-like material could be used to provide a gripping surface for the hand.

In other preferred embodiments, one or more aspects and features of the present invention are incorporated in each artificial hand disclosed in U.S. Pat. No. 7,655,051 as being representative of the invention therein. In this context, the pull cable may be manually actuated or mechanically actuated. Thus, for example, the pull cord is activated by a shoulder harness worn by the user, who, by movement of his or her shoulders, causes tension on the cord, thereby opening the prosthetic hand, or causes the tension in the cord to be relaxed, thereby closing the prosthetic hand. In an alternative, a mechanical arrangement, such as electric motors, can be used to pull or relax the cable.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

For example, while the artificial hand has been described as a prosthetic for use by a person, aspects and features of the invention are equally applicable in the context of robotic hands.

What is claimed is:

1. An artificial hand comprising:
   (a) a palm component including a plurality of finger sockets for receiving a plurality of artificial fingers; and
   (b) a plurality of artificial fingers removably engaged in a snap-fit manner in each of the plurality of finger sockets on the palm component, each one of the plurality of fingers comprising:
   (i) a locking slide including a plurality of locking teeth and a reverse lock including a locking cam, wherein the locking cam is adapted to be engaged with the locking teeth to lock the finger in such a manner as to prevent it from opening further, and
   (ii) a tie connected to the reverse lock and extending from an end of the finger engaged in the snap-fit manner, the tie engaging a mechanism disposed in the palm component such that tension can be applied to the tie via the palm component, wherein applying tension to the tie causes the locking cam to disengage the reverse lock and allow the finger to open.

2. The artificial hand of claim 1, wherein a thumb of the artificial hand is rotatable between a first position and a second position.

3. The artificial hand of claim 2, wherein the first position is configured for use with a "power" grip formation where the fingers are closed.

4. The artificial hand of claim 2, wherein the fingers include four fingers, and the first position is configured for use with a "fine" grip formation where three of the fingers are closed and one of the fingers is open.

5. The artificial hand of claim 2, wherein the second position is configured for use with a "lateral" grip formation where the fingers are closed.

6. The artificial hand of claim 2, wherein the fingers include four fingers, and the second position is configured for use with a "typing" grip formation where three of the fingers are closed and one of the fingers is open.

7. The artificial hand of claim 1, wherein the fingers are interchangeable.

8. The artificial hand of claim 1, wherein the artificial hand comprises a plurality of coil springs.

9. The artificial hand of claim 1, wherein the tie comprise a zip-tie connector.

10. An artificial hand comprising:
  (a) a palm component including a plurality of finger sockets for receiving a plurality of artificial fingers; and
  (b) a plurality of artificial fingers removably engaged in a snap-fit manner in each of the plurality of finger sockets on the palm component, each one of the plurality of fingers comprising:
    (i) a locking slide including a plurality of locking teeth and a reverse lock including a locking cam, wherein the locking cam is adapted to be engaged with the locking teeth to lock the finger in a plurality of discrete positions in such a manner as to prevent it from opening further, and
    (ii) a tie connected to the reverse lock and extending from an end of the finger engaged in the snap-fit manner, the tie engaging a mechanism disposed in the palm component such that tension can be applied to the tie via the palm component, wherein applying tension to the tie causes the locking cam to disengage the reverse lock and allow the finger to open.

11. The artificial hand of claim 10, wherein a thumb of the artificial hand is rotatable between a first position and a second position.

12. The artificial hand of claim 11, wherein the first position is configured for use with a "power" grip formation where the fingers are closed.

13. The artificial hand of claim 11, wherein the fingers include four fingers, and the first position is configured for use with a "fine" grip formation where three of the fingers are closed and one of the fingers is open.

14. The artificial hand of claim 11, wherein the second position is configured for use with a "lateral" grip formation where the fingers are closed.

15. The artificial hand of claim 11, wherein the fingers include four fingers, and the second position is configured for use with a "typing" grip formation where three of the fingers are closed and one of the fingers is open.

16. The artificial hand of claim 10, wherein the fingers are interchangeable.

17. The artificial hand of claim 10, wherein the artificial hand comprises a plurality of coil springs.

18. The artificial hand of claim 10, wherein the tie comprise a zip-tie connector.

\* \* \* \* \*